United States Patent [19]

Levin

[11] 4,262,032

[45] Apr. 14, 1981

[54] SWEETENED EDIBLE FORMULATIONS

[75] Inventor: Gilbert V. Levin, Chevy Chase, Md.

[73] Assignee: Biospherics Incorporated, Rockville, Md.

[21] Appl. No.: 838,211

[22] Filed: Sep. 30, 1977

Related U.S. Application Data

[63] Continuation-in-part of Ser. No. 683,157, May 4, 1976, abandoned, which is a continuation of Ser. No. 106,896, Jan. 15, 1971, abandoned, which is a continuation of Ser. No. 672,457, Oct. 3, 1967, abandoned.

[51] Int. Cl.$^3$ ............................................. A23L 1/09
[52] U.S. Cl. .................................. 426/658; 426/804; 424/361
[58] Field of Search .................... 426/658, 804; 536/1; 424/361

[56] References Cited

U.S. PATENT DOCUMENTS 3,278,314  10/1966  Colby et al. ............................ 426/90

OTHER PUBLICATIONS

Percival, *Structural Carbohydrate Chemistry*, 1962, London, J. Garnet Miller Ltd., pp. 2, 12, 16, 22, 24, 27 and 129.
Boyd et al., *Science*, 137 (1962) p. 669.
Chemical Abstracts 63:10314g.
*The Merck Index of Chemicals and Drugs*, 7th Edition, Merck & Co., Inc., Rahway, N.J., (1960), pp. 503, 969.
Pigman, *The Carbohydrates*, Academic Press, Inc., New York, (1957), p. 800.

*Primary Examiner*—Esther M. Kepplinger
*Attorney, Agent, or Firm*—Roylance, Abrams, Berdo & Farley

[57] ABSTRACT

This disclosure is concerned with a variety of methods for preparing various L-hexose monosaccharides and organoleptic testing in regard to the sweetness of these saccharides. The disclosure is further concerned with the use of these L-hexose monosaccharides as sweetening agents in a wide variety of foodstuffs and other edible formulations. The L-hexose monosaccharides disclosed include L-glucose, L-allose, L-fructose, L-gulose, L-galactose, L-altrose, L-idose, L-talose, L-tagatose and L-psicose.

11 Claims, No Drawings

SWEETENED EDIBLE FORMULATIONS

This application is a continuation-in-part of application Ser. No. 683,157, filed May 4, 1976; now abandoned which was a continuation of application Ser. No. 106,896, filed Jan. 15, 1971 (now abandoned); which was a continuation of application Ser. No. 672,457, filed Oct. 3, 1967 (now abandoned).

This invention is concerned with foodstuffs and other edible formulations containing sweetening agents which are of particular value in the treatment or prevention of obesity or other conditions in which the normal function of the body in regard to carbohydrate metabolism is impaired.

More particularly, this invention is concerned with the preparation of foodstuffs having properties such as appetizing appearance, texture and taste, which are similar to those associated with the common sugar sweetening agents. However, the foodstuffs and other edible formulations prepared according to this invention will not have the deleterious effects, in some people, that are associated with those foodstuffs prepared with the common sugar sweetening agents. Thus, this invention is concerned with the sweetening of foodstuffs and other edible formulations with novel sweetening agents comprising the L-hexose monosaccharides. These sweetening agents are unique in that their physical properties are similar to those of the natural sugars used as sweetening agents, but as opposed to the common sugars, these compounds are either not metabolized by the body or are metabolized to such a small extent, that they do not impart to the body the detrimental effects that some people have due to the improper metabolization of the common sugar sweetening agents.

It is well known that the intake of certain carbohydrates, and in particular D-glucose, and certain oligosaccharides, particularly those converted to D-glucose, such as sucrose, must be carefully regulated or entirely restricted in people suffering from conditions such as diabetes mellitus and similar conditions wherein the function of the pancreas is impaired in regard to carbohydrate metabolism. A similar situation also exists in persons in the treatment or prevention of obesity.

Numerous proposals have been made in the prior art to provide a suitable means for the sweetening of foods for persons who must restrict their intake of metabolizable carbohydrates. However, these prior art methods are definitely deficient in several respects and hence, cannot be considered as ideal non-nutritive sweetening agents. For example, the commonly used artificial sweetening agents, such as saccharin, cyclamates and mixtures leave a bitter and objectional aftertaste, after foods sweetened with these have been eaten. Likewise, since they are used in very minute amounts, due to their high degree of sweetness, various bulking agents must be added to serve as a carrier and, in some cases, replace the bulk normally supplied by the replaced sugar. The use of bulking agents is particularly necessary in situations wherein solid foods, such as breads, cakes, cookies, cake-icing, solid and semi-solid candles and chewing gum are to be prepared, since it is practically impossible to prepare this type of food with a wholesome and appetizing appearance without the use of some bulking agent to replace the volume of normal sugar, which is not required by the use of artificial sweetness. However, the use of various bulking agents presents difficulties in that those most effective in replacing the bulk of the normal sugar are for the most part based upon carbohydrates, which are metabolized by the body and, hence, have some nutritive value.

According to the present invention, the use of certain L-hexose monosaccharides as sweetening agents alleviates the problems of the prior art sweetening agents.

These novel sweetening agents have no bitter and objectional aftertaste, and, further, since they have practically the same physical properties and appearance as the normal sugars used as sweetening agents, the problem of the use of carriers, and bulking agents to improve the appearance of foodstuffs prepared therefrom is negated.

The ability of the subject L-hexoses to function as sweetening agents is unique, in view of reports in the prior art as to their property of being non-sweet and having a salty taste.

Due to the fact that these L-hexose monosaccharides are either not metabolized by the body or they are metabolized to such a small extent, they will have little or no effect upon the normal body functions. Consequently, these new sweetening agents may ideally be used in foodstuffs and other edible formulations designed for persons whose metabolizable carbohydrate intake must be restricted because of conditions such as diabetes mellitus or obesity.

Another outstanding feature of the use of the subject L-hexose sweetening agents, is that formulations prepared using them as sweetening agents are less susceptible to spoilage due to the growth of various microorganisms than those prepared with the conventional saccharide sweetening agents. For example, one large problem encountered with the use of formulations such as syrups, prepared from conventional saccharide sweetener such as in the soft drink industry, is the decomposition due to bacterial growth. Since the L-hexose saccharide sweetening agents of the present invention provide little or no nutrient value for the various microorganisms, their growth and, hence, the corresponding spoilage of these formulations is drastically reduced.

Other advantages of the subject L-hexose sweetening agents are that they are non-calorific and are believed to be non-carcinogenic. Thus, they are suitable substitutes for sugar for persons on a reducing diet, and they probably do not possess the carcinogenic disadvantages associated with saccharin and cyclomates.

The term L-hexose monosaccharides as used herein is used within the meaning of the standard terminology of carbohydrate chemists. Thus, for example, one particularly effective sweetening agent according to this invention is L-glucose, which is a stereoisomer of the widely known sweetening agent D-glucose. The D- and L-prefixes are used to denote the configuration of the hexose structure according to the universally accepted Fisher system of nomenclature as modified by Rosanoff. This may be further exemplified by reference to the following structural formulas:

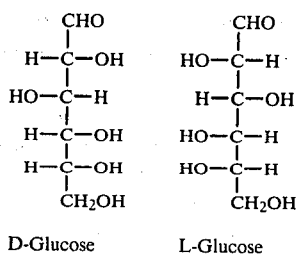

D-Glucose    L-Glucose

As may be ascertained from these formulas, these two compounds are mirror images of one another. The prefixes of D- and L- are not to be confused with d- and l-, which are used to denote the direction of optical rotation, i.e., d(dextro-) or l(levo-). This is discussed more fully below.

As is common in the art, the term hexose is inclusive of those six carbon sugars or monosaccharides, wherein the carbonyl group is either in the aldehyde form (aldoses) or the keto form (ketoses) and monosaccharide refers to the simple or uncombined sugar. Typical examples of these aldoses or aldohexoses are L-talose, L-galactose and L-allose, while typical examples of these ketoses or ketohexoses are L-tagatose and L-psicose.

A better understanding of the products and processes of this invention may be obtained from the examples given below, which disclose the best mode presently contemplated by the inventor of carrying out this invention.

EXAMPLE 1

L-Glucose

A solution of 50 grams of β-L-arbinose and 180 ml. of nitromethane in 100 ml. of absolute methanol was heated in a 3-neck, 1-liter flask with a solution of 10.5 grams of 350 ml. of absolute methanol. The reaction mixture was protected from moisture, refluxed and stirred for 18–20 hours. The resulting precipitate of sodium aci-nitroalcohols was collected by filtration and washed with cold methanol and then with petroleum ether. The moist salts were then dissolved in 400 ml. of cold (0° C.) water and the solution immediately deionized by passage through a column containing 400 ml. of Dowex-50(H+) resin. The effluent and washings were concentrated at reduced pressure with several portions of absolute ethanol to remove residual water. The resulting crystals were filtered with the aid of cold ethanol and the filtrate reworked to provide two additional crops of crystals. This yielded approximately 55 grams of crude mixed nitroalcohols. This crude product was separated by fractional crystallization from ethanol. The less soluble fraction was 1-deoxy-1-nitro-L-mannitol, m.p. 133°–134° C. (18 gr.) and the more soluble fraction 1-deoxy-1-nitro-L-glucitol, m.p. 104°–106° C. (15 gr.).

A solution of 5 grams of 1-deoxy-1-nitro-L-glucitol dissolved in 15 ml. of 2 N sodium hydroxide was added dropwise to a stirred solution of 7.5 ml. of sulfuric acid in 9 ml. of water at room temperature. After dilution with 200 ml. of water, the solution was neutralized to Congo red indicator with warm barium hydroxide solution and the remaining sulfate ion precipitated with barium acetate solution. The barium sulfate was removed by filtration and the filtrate de-ionized by passage through 50 ml. of Dowex-50(H+) resin. The effluent and washings were concentrated at reduced pressure to a syrup. This syrup was diluted with a few drops of ethanol and allowed to crystallize. The resulting β-L-glucose was filtered with the aid of ethanol; yield 2.5 grams, mp 146°–147° C.

EXAMPLE 2

β-L-Allose

A solution of 13 grams of L-allono-1,4-lactone [Austin and Humdles, JACS 56 1152 (1934), Hudson et al, ibid 56 1248 (1934)] in 100 ml. of water was cooled at 0° C. in an ice-salt mixture. This was reduced by adding to the lactone solution small amounts of a 2.5% sodium amalgam. During the reduction, the reaction mixture was maintained on the acid side of Congo red (pH 5) by the intermittent addition of 20% sulfuric acid, as needed. The reaction mixture was agitated vigorously during this step to prevent the formation of local zones of alkalinity. Periodically, small aliquots of the reaction mixture were withdrawn and tested for reducing sugar content. Approximately 400 grams of the 2.5% sodium amalgram were needed to produce the maximum quantity of reducing sugar. After the addition of the sodium amalgram, the aqueous phase was decanted from the mercury, filtered and hot ethanol added with stirring to bring the final concentration to 85%. The precipitated sodium sulfate was removed by filtration and the filtrate concentrated to about 50 ml. at reduced pressure and at a temperature less than 45° C. This filtrate was poured through a pad of activated carbon and then titrated with a one-half saturated solution of barium hydroxide using phenolphthalein as an indicator. The reaction mixture was poured into ten volumes of hot, absolute ethanol and the resulting barium L-allonate, which is insoluble in 93% ethanol, was filtered. The filtrate was evaporated under reduced pressure to a thin syrup and allowed to crystallize. Crystals were separated by filtration, the filtrate and washings were concentrated to a thin syrup and an additional crop of β-L-allose was obtained upon storage in a desicator. This gave a yield of about 70%. Recrystallization was effected from hot 93% ethanol to yield pure crystals, m.p. 128°–129° C.

EXAMPLE 3

β-L-Fructose Hemihydrate

1-Deoxy-1-diazo-keto-L-fructose tetracetate

A solution of 14 grams of tetra-O-acetyl-L-arabinoyl chloride [Wolfrom and Thompson, J. Am. Chem. Soc., 68 791 (1961)] in 200 ml. of absolute ether was added slowly to a solution of 4.2 grams of diazomethane in 500 ml. of absolute ether. The resulting solution was allowed to stand for about two hours at room temperature and then concentrated approximately to one-third its volume. The product was crystallized by the addition of petroleum ether with cooling and yielded about 10 grams (65% yield) of crude product. Pure product was obtained by recrystallization from absolute ethanol, melting point 93°–94° C.

Keto-L-fructose pentacetate

A solution of 10 grams of 1-deoxy-1-diazo-keto-L-fructose tetracetate and 0.01 gram of cupric acetate in 300 ml. of anhydrous acetic acid in a 2 liter flask was heated gently and after the initial violent evolution of gas had subsided, was brought just to the boiling point. The solvent was removed by distillation under reduced pressure, the final portion was removed by distillation with ethanol. The resulting syrup was dissolved in 15 ml. of ethanol, filtered and allowed to crystallize overnight in a refrigerator. This yielded 4 grams of crystals, m.p. 65° C. The syrup obtained from mother liquid was dissolved in 50 ml. of acetic anhydride containing 0.5 gram of zinc chloride (fresh fused), allowed to stand overnight at room temperature and heated 90 minutes at 50° C. Excess acetic anhydride was hydrolyzed by pouring into 200 ml. of ice-water and stirred for 2 hours. The acetylated sugar was extracted from the water with 200 ml. of chloroform. The chloroform solution was washed with water, dried over anhydrous sodium sulfate, filtered and evaporated to a syrup. This syrup was crystallized from 10 ml. of ethanol and yielded an additional 3 grams of product.

β-L-fructose hemihydrate

Ten grams of finely powdered keto-L-fructose pentacetate was added to 135 ml. of an aqueous solution of 13 grams of barium hydroxide octahydrate at 0° C. This mixture was stirred at this temperature of about 30 minutes at which time all of the pentacetate was dissolved, and then allowed to stand for an additional 90 minutes at this temperature. A solution of 3 grams of oxalic acid in 25 ml. of water was added to precipate most of the barium ions. The remainder of the barium ions were removed by stirring the filtered solution with excess of Amberlite IR-100(H+) cation-exchange resin until the solution no longer gave a positive test for barium ions with sulfate. The resin was removed by filtration and the solution was stirred with Duolite A-4(OH−) anion-exchange resin until the pH increased to the range of 6.8 to 7. The resin was filtered off and the solution concentrated under reduced pressure at a temperature below 50° C. The resulting syrup was crystallized from ethanol at refrigerator temperature to yield about 4 grams of product. This was recrystallized as β-L-fructose hemihydrate by dissolving in a small amount of water, evaporating under reduced pressure and dissolving the syrup in ethanol; melting point 101°–103° C.

EXAMPLE 4

L-Gulose

2,4-O-Benzylidene-6-deoxy-6-nitro-D-glucitol

A solution of 53.7 grams of syrupy 2,4-O-benzylidene-L-xylose [Fischer and Piloty, Ber. 24 52 (1891)] in one liter of absolute methanol and 160 ml. of nitromethane was treated with a solution of 10 grams of metallic sodium in 800 ml. of absolute methanol of 22 hours at room temperature. The reaction mixture was acidified with a slight excess of glacial acetic acid and concentrated under reduced pressure. Methanol and nitromethane were removed by the addition of water and further concentrated under reduced pressure. The moist crystalline mass was mixed with cold (0° C.) water, filtered and washed with cold (0° C.) water. This yielded 34 grams (50% yield) of crude 2,4-O-benzylidene-6-nitro-D-glucitol, m.p. 178°–181° C.; recrystallization gave a purer product, m.p. 192°–194° C.

6-Deoxy-6-nitro-D-glucitol

Ten grams of 2,4-benzylidene-6-deoxy-6-nitro-D-glucitol was heated for one hour at 75°–80° C. with 100 ml. of 0.1 N $H_2SO_4$. After cooling the solution was extracted three times with ether to remove the benzaldehyde and neutralized with excess barium carbonate. The barium carbonate and barium sulfate were removed by centrifugation and filtration through a precoated filter. The clear solution was then concentrated under reduced pressure to a syrup, which crystallized spontaneously after standing several days. This product was recrystallized from ethyl acetate containing a little methanol and yielded 5.6 grams (79% yield) of 6-deoxy-6-nitro-D-glucitol, m.p. 78°–80° C. On recrystallization from dry ethyl acetate, there were obtained soft needles, m.p. 81°–83° C., and hard compact prisms, m.p. 89°–91° C.

L-Glucose Benzylphenylhydrazone

A syrup of 6-deoxy-6-nitro-D-glucitol which was obtained by the hydrolysis of 13.6 grams of 2,4-benzylidene-6-deoxy-6-nitro-D-glucitol was dissolved in 55 ml. of 1 N sodium hydroxide. This solution was added dropwise to 20 ml. of vigorously stirred sulfuric acid solution (60% weight/weight). The acidic solution was then diluted with water and neutralized with excess barium carbonate, 4 ml. of acetic acid were added and the barium sulfate was removed by filtration. The clear filtrate was concentrated under reduced pressure to a syrup which was dissolved in 100 ml. of 75% ethanol. The ethanolic solution was filtered and treated with about 10 grams of 1-benzyl-1-phenylhydrazine. This solution was allowed to evaporate in an open dish with the occasional addition of small amounts of methanol, until crystallization was complete. The crystals were freed from the syrup by washing with water and then ether. This yielded 8.5 grams (67% yield) of crude L-gulose benzylphenylhydrazone, m.p. 124°–128° C. This was recrystallized from a solution of 110 ml. of chloroform and 15 ml. of methanol to give colorless L-gulose benzylphenylhydrazone, m.p. 130°–131° C.

L-Gulose

The L-gulose benzylphenylhydrazone was refluxed for three hours with 100 ml. of water and 20 ml. of ethanol containing 7.5 ml. of benzaldehyde and 0.8 grams of benzoic acid. After cooling, the solution was decanted from the crystals of benzaldehyde benzylphenylhydrazone and extracted several times with ether to remove the benzaldehyde and benzoic acid. The solution was then decolorized with activated carbon and concentrated under reduced pressure to a colorless syrup to yield 3.4 grams of syrupy L-gulose.

EXAMPLE 5

α-L-Galactose

L-Galactono-1,4-lactone

A solution of 21.6 grams (0.1 mole) of sodium D-galacturonate [Molten, et al, J. Am. Chem. Soc., 61 270 (1939); Pigman, J. Research Natl. Bur. Standards, 25 301 (1940); Isbell et al, ibid 32 77 (1974)] in 200 ml. of water was placed in a 500 ml. flask and cooled in an ice bath. With stirring, 100 ml. of cold, freshly-prepared 0.5 M. aqueous solution of sodium borohydride (100% excess) was added and the reduction mixture allowed to stand overnight at about 5° C. It was then stirred with 25 ml. of cation-exchange resin, Amberlite I.R.-120(H+) to decompose unreacted sodium borohydride, and then poured through a column containing 250 ml. of resin. The effluent and washings were concentrated under reduced pressure to a syrup. Methanol was added to the syrup and this mixture warmed under reduced pressure to remove the boric acid as methyl borate. This procedure was repeated two times. The residue was then heated with 25 ml. of Methyl Cellusolve (2-methoxyethanol) on a boiling water bath for two hours. Isopropanol was added almost to the point of incipient turbidity and the solution seeded with crystalline L-galactone-1,4-lactone. Crystals of L-galactono-1,4-lactone were separated. Concentration of the mother liquor and addition of isopropanol gave more crystalline lactone. Recrystallization from hot ethanol gave about a 90% yield of crystalline L-galactone-1,4-lactone, m.p. 134° C.

L-Galactose

A mixture of 500 ml. of finely crushed ice, 115 grams of sodium hydrogen oxalate and 10 grams of L-galactone-1,4-lactone was agitated in a closely covered, high speed blender with stainless steel blades. After a few seconds of blending, 260 grams of pellets of 5% sodium-amalgam was gradually added and agitation was continued for 15 minutes, during which time the temperature rose to about 30°-35° C. The resulting solution was decanted from the mercury and neutralized with dilute sodium hydroxide until a faint but permanent pink color of phenolphthalein was obtained. This solution was evaporated under reduced pressure to a volume of about 100 ml. and treated with five volumes of methanol. The precipitated salts were separated, washed with a little methanol and discarded. The filtrate was concentrated under reduced pressure to about 50 ml. and again treated with five volumes of methanol. The precipitated salts were again removed by filtration and the solution after concentration to about 50 ml. was deionized by passage through a column containing 60 ml. of mixed cation and anion exchange resins, Amberlite I.R. −120(H+) and Duolite A 4(OH−). The combined effluent and washings were tested for ionic impurities by means of a conductivity meter and, when free of ionic impurities, concentrated under reduced pressure to a thin syrup. This syrup was dissolved in a minimal amount of methanol and isopropanol added to the point of incipient turbidity. The crop of crystals was separated and washed with methanol, and an additional crop of crystals obtained from the mother liquor by concentration and addition of methanol to give a total yield of about 80%.

Organoleptic tests were conducted to determine the sweetening power of the L-hexoses. Exemplary of these is the following conducted with D-glucose, L-glucose and sucrose (common sugar), wherein distilled water solutions of both D-glucose and sucrose in concentrations of 1 mg./ml., 10 mg./ml. and 100 mg./ml. were prepared. Each of these solutions was divided into three parts and each tested by a panel of three tasters. Each member of the panel sampled each of the two solutions at the three different concentrations, with appropriate rinsing of their mouths after each taste. The panel had previously been instructed to rate each of the samples on the basis of 0 to 3, the 0 indicating no sweetness and the 3 indicating the highest degree of sweetness. The panel was in agreement that a substantial degree of sweetness, i.e., in the range of 2-3, was not attained by either the D-glucose or sucrose until the more concentrated, i.e., 100 mg./ml., solutions were tasted. This same panel was used to taste test solutions of L-glucose at a concentration of 100 mg./ml. using the same procedure. Again, the panel was in agreement that the L-glucose solution was sweet and a substantial degree of sweetness, i.e., a 2-3 rating, was obtained with the 100 mg./ml. solutions of L-glucose. Similar results were obtained with the other L-hexose monosaccharides of this invention. Thus, the minimum concentration of L-hexose necessary to obtain a substantial degree of sweetness is about 100 mg./ml.

The above examples are indicative of the methods which may be used to obtain the L-hexose monosaccharides used in the present invention. Obviously, other preparation methods may be employed to obtain the subject L-hexoses used as sweetening agents within the scope of the present invention. Other 2-aldohexoses which may be used according to this invention as sweetening agents to prepare edible food formulations include L-altrose, which may be prepared from L-arabinose via the intermediate formation of L-ribose and L-altronic acid [Austin et al., J. Am. Chem. Soc., 56 1153 (1934)], L-idose, which may be prepared from D-glucose [Meyer et al., Helv. 29 152 (1946)], and L-talose, which may be prepared according to the procedure of Stallhaar and Reichstein, Helv. 21 3 (1938). Other L-ketohexoses which may be used as sweetening agents include L-tagatose, which may be prepared by the alkaline rearrangement of L-sorbose and L-psicose, which may be prepared by the oxidative fermentation of allitol by sorbose bacterium [Steiger et al, Helv. 18 790 (1935)].

Other commonly known and employed preparative methods may be used to prepare the L-hexose monosaccharides of the present invention. Discussions of such methods may be found in the literature of carbohydrate chemistry. For example, one general method of preparing hexoses is based upon the lengthening of the carbon-to-carbon chain, i.e., preparation of hexoses from the corresponding pentose. Under this general method are procedures such as the cyanohydride synthesis (Kiliani-Fischer method), nitromethane synthesis (Sowden-Fischer method), and diazomethane synthesis, and each of these are useful in the preparation of the subject hexoses. Another general method involves a shortening of the carbon-to-carbon chain, i.e., preparation of hexoses from the corresponding heptose. Under the general method are procedures such as the Ruff degradation, the Wohl degradation, the Weeman degradation, the MacDonald-Fischer degradation and the Weygand-Lowenfeld degradation and each of these are useful in the preparation of the subject L-hexoses. Another general method involves changing the configuration of the corresponding saccharide. Thus, procedures such as the pyridine and alkaline rearrangement and glycol synthesis are useful. Discussions of the methods may be found in W. Pigman, *The Carbohydrates,* pages 106–132 (Academic Press, New York, 1957), and the references cited therein.

As has been discussed above, the term L-hexose monosaccharides as used herein and in the appended claims is used within the standard meaning in the art. Thus, the prefix "L" refers to the configuration of the hexose structure according to the Fischer system of nomenclature as modified by Roranoff. According to this system, the subject L-hexoses are considered to be those derived from the fundamental structural glycerose, L-glyceraldehyde of the formula:

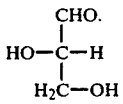

by the successive application of the cyanohydrin synthesis to obtain a hexose. These compounds are configurationally the direct opposite of those hexoses derived by the same series of reactions, from the fundamental structural glycerose, D-glyceraldehyde of the formula:

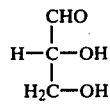

Similarly, the subject L-ketohexoses are, according to this system, derived from the fundamental L-ketose, L-erythrulose (L-threulose) of the formula:

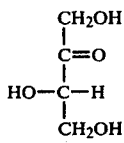

A further discussion of this terminology may be found in W. Pigman, *The Carbohydrates,* pages 21–29 (Academic Press, New York, 1957) and the references cited therein. It is, of course, to be understood that while the configuration of the L-hexoses, in particular L-glucose, has been shown structurally in an open chain of Fischer projection type formula, it is equally within the scope of this invention that the L-hexoses may have a ring structure, for example, a pyranose or furanose ring, with the L-configuration, and still be useful as sweetening agents for edible formulations.

As has been discussed above, the L-hexose monosaccharides are sweet, soluble in water and stable in aqueous solutions. Therefore, they are useful for sweetening all types of materials which are intended for consumption or at least contact with the mouth of the user, such materials being herein generically designated as edible materials or foodstuffs. Typical illustrative examples of edible foodstuffs which may be sweetened according to this invention are fruits, vegetables, juices or other liquid preparations made from fruits or vegetables, meat products, particularly those conventionally treated with sweetened liquors, such as bacon and ham, milk products such as chocolate dairy drinks, egg products, such as egg nogs, custards, angel food mixes, salad dressings, pickles and relishes, ice creams, sherberts and ices, ice milk products, bakery products, icings, confections and confection toppings, syrups and flavors, cake and pastry mixes, beverages, such as carbonated soft drinks, fruit aids, wines, dietary-type foods, cough syrups and other medicinal preparations such as pastes, powders, foams and denture-retaining adhesives, mouth washes and similar oral antiseptic liquids, tobacco products, adhesives for gumming stamps, envelopes, labels and the like.

In using the sweetening agents of this invention, they are incorporated in the material to be sweetened in the amount required to attain the desired level of sweetness. It is obvious that there is nothing critical about the concentration of sweetening agent which is used. It is simply a matter of attaining a desired sweetness level appropriate to the material in question. Moreover, the technique of sweetening materials with the compounds of the invention offers no difficulty as the sweetening agent is simply incorporated with the material to be sweetened. The sweeteners may be added directly to the material or they may be first incorporated with a diluent to increase their bulk and added to the material. As diluent, if needed, one may use liquid or solid carriers, such as water, glycol, starch, sorbitol, salt, citric acid or other non-toxic substances compatible with the material to be sweetened.

While the invention has been described as mainly concerned with foodstuffs and other non-toxic formulations for human consumption, it is obviously within the scope of this invention that these sweetened compositions may be used for consumption by other animals, such as farm and domestic animals.

While the invention has been described with respect to the use of L-hexose monosaccharides as the sole sweetening agent, it is to be understood that they may be used in combination with conventionally used sweetening agents, e.g., in combination with a minor amount of sucrose.

I claim:

1. A process for the preparation of a sweetened edible formulation in which the sweetening agent is non-calorific and less susceptible to spoilage due to the growth of microorganisms which comprises the step of mixing a food stuff with an amount sufficient to sweeten said food stuff of an L-hexose monosaccharide selected from the group consisting of L-glucose, L-allose, L-fructose, L-gulose, L-galactose, L-altrose, L-idose, L-talose, L-tagatose and L-psicose as a sweetening agent.

2. A process as defined in claim 1 wherein said L-hexose monosaccharide is L-glucose.

3. A process as defined in claim 1 wherein said L-hexose monosaccharide is L-allose.

4. A process as defined in claim 1 wherein said L-hexose monosaccharide is L-fructose.

5. A process as defined in claim 1 wherein said L-hexose monosaccharide is L-gulose.

6. A process as defined in claim 1 wherein said L-hexose monosaccharide is L-galactose.

7. A process as defined in claim 1 wherein said L-hexose monosaccharide is L-altrose.

8. A process as defined in claim 1 wherein said L-hexose monosaccharide is L-idose.

9. A process as defined in claim 1 wherein said L-hexose monosaccharide is L-talose.

10. A process as defined in claim 1 wherein said L-hexose monosaccharide is L-tagatose.

11. A process as defined in claim 1 wherein said L-hexose monosaccharide is L-psicose.

* * * * *